US008903472B2

(12) United States Patent
Kassab (10) Patent No.: US 8,903,472 B2
(45) Date of Patent: Dec. 2, 2014

(54) APPLICATIONS OF SCALING LAWS OF TREE STRUCTURES

(75) Inventor: Ghassan S. Kassab, Zionsville, IN (US)

(73) Assignee: DTherapeutics, LLC, San Diego, CA (US)

( * ) Notice: Subject to any disclaimer, the term of this patent is extended or adjusted under 35 U.S.C. 154(b) by 877 days.

(21) Appl. No.: 12/522,350

(22) PCT Filed: Jan. 22, 2008

(86) PCT No.: PCT/US2008/000762
§ 371 (c)(1),
(2), (4) Date: Jul. 7, 2009

(87) PCT Pub. No.: WO2008/091568
PCT Pub. Date: Jul. 31, 2008

(65) Prior Publication Data
US 2010/0041981 A1    Feb. 18, 2010

Related U.S. Application Data

(60) Provisional application No. 60/881,833, filed on Jan. 23, 2007.

(51) Int. Cl.
| *A61B 5/05* | (2006.01) |
| *A61B 5/02* | (2006.01) |
| *A61B 6/00* | (2006.01) |
| *A61B 5/026* | (2006.01) |
| *A61B 5/055* | (2006.01) |
| *A61B 6/03* | (2006.01) |

(52) U.S. Cl.
CPC ............... *A61B 6/504* (2013.01); *A61B 5/055* (2013.01); *A61B 6/03* (2013.01); *A61B 5/02007* (2013.01); *A61B 5/026* (2013.01)
USPC ............. 600/427; 600/411; 600/431; 702/19; 703/11

(58) Field of Classification Search
USPC .......... 600/410, 419, 481, 485, 504; 382/128, 382/131; 128/923; 703/11
See application file for complete search history.

(56) References Cited

U.S. PATENT DOCUMENTS

| 6,260,021 B1 * | 7/2001 | Wong et al. ....................... 705/2 |
| 6,261,233 B1 | 7/2001 | Kantorovich |
| 7,069,068 B1 | 6/2006 | Ostergaard |
| 2005/0059876 A1 * | 3/2005 | Krishnan et al. .............. 600/407 |
| 2006/0235669 A1 | 10/2006 | Charbel et al. |

OTHER PUBLICATIONS

Zhou et al., "In vivo validation of the design rules of the coronary arteries and their application in the assessment of diffuse disease" Physics in Medicine and Biology, vol. 47, pp. 977-993, 2002.*
Kassab et al. "On the design of the coronary arterial tree: a generalization of Murray's law", Physics in Medicine and Biology, vol. 44, pp. 2929-2945, 1999.*
PCT/US2008/000762, PCT Search Report and Written Opinion, dated Aug. 29, 2008.

* cited by examiner

*Primary Examiner* — Unsu Jung
*Assistant Examiner* — Joseph M Santos Rodriguez
(74) *Attorney, Agent, or Firm* — Reichel IP LLP; Mark C. Reichel; Natalie J. Dean (57) ABSTRACT

In at least one embodiment, a method for diagnosing vascular disease is provided, the method comprising the steps of obtaining a vessel image showing a vasculature of a vessel, identifying at least two measurements from the vasculature of the vessel, the measurements relating to at least two parameters, calculating a relationship between the at least two parameters from the at least two measurements to generate one or more vasculature data points, and comparing the one or more vasculature data points to data relative to a model vasculature to determine the extent of vascular disease. In an another embodiment, a method for diagnosing vascular disease in a patient's vascular tree is provided, the method comprising the steps of generating a model vascular tree from a minimum energy hypothesis calculation, and comparing the patient's vascular tree with the model vascular tree to determine the extent of vascular disease.

62 Claims, 3 Drawing Sheets

APPLICATIONS OF SCALING LAWS OF TREE STRUCTURES

PRIORITY

The present application is related to, and claims the priority benefit of, International Patent Application Serial No. PCT/US2008/000762, filed Jan. 22, 2008, which is related to, and claims the priority benefit of, U.S. Provisional Patent Application Ser. No. 60/881,833, filed Jan. 23, 2007. The contents of each of these applications are hereby incorporated by reference in their entirety into this disclosure.

BACKGROUND

The disclosure of the present application relates generally to diagnosis of vascular disease, in particular relating to using morphological features of the coronary artery tree to diagnose coronary artery disease.

Diffuse coronary artery disease (DCAD), a common form of atherosclerosis, is difficult to diagnose because the arterial lumen cross-sectional area is diffusely reduced along the length of the vessels. Typically, for patients with even mild segmental stenosis, the lumen cross-sectional area is diffusely reduced by 30 to 50%. The failure of improved coronary flow reserve after angioplasty may mainly be due to the coexistence of diffuse narrowing and focal stenosis. Whereas angiography has been regarded as the "gold standard" in the assessment of focal stenosis of coronary arteries, its viability to diagnose DCAD remains questionable. The rationale of conventional angiography in the assessment of coronary artery disease is to calculate the percent lumen diameter reduction by comparison of the target segment with the adjacent 'normal' reference segment. In the presence of DCAD, however, an entire vessel may be diffusely narrowed so that no true reference (normal) segment exists. Therefore, in the presence of DCAD, standard angiography significantly underestimates the severity of the disease.

To overcome the difficulty of using angiography in the diagnosis of DCAD, intravascular ultrasound (IVUS) has been the subject of extensive studies. IVUS has the advantage of directly imaging the cross-sectional area along the length of the vessel using a small catheter. The disadvantage of IVUS, however, is that its extensive interrogation of diseased segments may pose a risk for plaque rupture.

What is needed is an improved approach to diagnosis and prognosis of vascular disease and its symptoms that avoid intrusive and expensive methods while improving accuracy and efficacy.

BRIEF SUMMARY

The disclosure of the present application addresses the need in multiple applications by the application of derived equations that can be used to diagnose disease as well as aid in the efficient fabrication of micro-fluidic channel devices.

In at least one embodiment of a method for diagnosing vascular disease according to the present disclosure, the method comprises the steps of obtaining a vessel image showing a vasculature of a vessel, identifying at least two measurements from the vasculature of the vessel, the measurements relating to at least two parameters, calculating a relationship between the at least two parameters from the at least two measurements to generate one or more vasculature data points, and comparing the one or more vasculature data points to data relative to a model vasculature to determine the extent of vascular disease. In another embodiment, the vessel image is an image selected from the group consisting of an angiograph, a CT image, and an MRI. In yet another embodiment, the at least two parameters comprise parameters relating to volume and length from the vasculature of the vessel.

In at least one embodiment of a method for diagnosing vascular disease according to the present disclosure, the step of calculating a relationship between the at least two parameters is performed using a volume-length relation. In another embodiment, the step of calculating a relationship between the at least two parameters is performed using a resistance-length and volume relation. In yet another embodiment, the at least two parameters comprise parameters relating to diameter and length from the vasculature of the vessel. In an additional embodiment, the step of calculating a relationship between the at least two parameters is performed using a diameter-length relation.

In at least one embodiment of a method for diagnosing vascular disease according to the present disclosure, the at least two parameters comprise parameters relating to flow rate and diameter from the vasculature of the vessel. In another embodiment, the step of calculating a relationship between the at least two parameters is performed using a flow rate-diameter relation. In yet another embodiment, the at least two parameters comprise parameters relating to resistance, length, and volume from the vasculature of the vessel. In an additional embodiment, the step of calculating a relationship between the at least two parameters is performed using a resistance-length and volume relation.

In at least one embodiment of a method for diagnosing vascular disease according to the present disclosure, the at least two parameters comprise parameters relating to flow rate and length from the vasculature of the vessel. In another embodiment, the step of calculating a relationship between the at least two parameters is performed using a flow rate-length relation. In yet another embodiment, the step of comparing the one or more vasculature data points to data relative to a model vasculature is performed by graphically comparing said data points to data relative to a model vasculature to determine the extent of vascular disease by identifying graphical differences between said data points to data relative to a model vasculature. In an additional embodiment, the step of comparing the one or more vasculature data points to data relative to a model vasculature is performed by comparing said data points to data relative to a model vasculature in table form to determine the extent of vascular disease by identifying numerically calculated differences between said data points to data relative to a model vasculature.

In at least one embodiment of a method for diagnosing vascular disease according to the present disclosure, the method comprises the steps of generating a model vascular tree from a minimum energy hypothesis calculation, and comparing the patient's vascular tree with the model vascular tree to determine the extent of vascular disease. In another embodiment, the step of generating a model vascular tree from a minimum energy hypothesis calculation further comprises the step of calculating a relationship between at least two parameters from at least two measurements to generate one or more model vasculature data points within the model vascular tree. In yet another embodiment, the at least two parameters comprise parameters relating to volume and length. In an additional embodiment, the step of calculating a relationship between the at least two parameters is performed using a volume-length relation. In a further embodiment, the step of calculating a relationship between the at least two parameters is performed using a resistance-length and volume relation.

In at least one embodiment of a method for diagnosing vascular disease according to the present disclosure, the at least two parameters comprise parameters relating to diameter and length. In another embodiment, the step of calculating a relationship between the at least two parameters is performed using a diameter-length relation. In yet another embodiment, the at least two parameters comprise parameters relating to flow rate and diameter. In an additional embodiment, the step of calculating a relationship between the at least two parameters is performed using a flow rate-diameter relation.

In at least one embodiment of a method for diagnosing vascular disease according to the present disclosure, the at least two parameters comprise parameters relating to resistance, length, and volume. In another embodiment, the step of calculating a relationship between the at least two parameters is performed using a resistance-length and volume relation. In yet another embodiment, the at least two parameters comprise parameters relating to flow rate and length. In an additional embodiment, the step of calculating a relationship between the at least two parameters is performed using a flow rate-length relation.

In at least one embodiment of a method for diagnosing vascular disease according to the present disclosure, the step of comparing the patient's vascular tree with the model vascular tree to determine the extent of vascular disease is performed by graphically comparing the patient's vascular tree with the model vascular tree to determine the extent of vascular disease by identifying graphical differences between the patient's vascular tree with the model vascular tree. In another embodiment, the step of comparing the patient's vascular tree with the model vascular tree to determine the extent of vascular disease is performed by comparing the patient's vascular tree with the model vascular tree in table form to determine the extent of vascular disease by identifying numerically calculated differences between the patient's vascular tree with the model vascular tree.

In at least one embodiment of a system for diagnosing vascular disease according to the present disclosure, the system comprises a processor, a storage medium operably connected to the processor, the storage medium capable of receiving and storing data relative of measurements from a vasculature of a vessel, wherein the processor is operable to obtain a vessel image showing a vasculature of a vessel, identify at least two measurements from the vasculature of the vessel, the measurements relating to at least two parameters, calculate a relationship between the at least two parameters from the at least two measurements to generate one or more vasculature data points, and compare the one or more vasculature data points to data relative to a model vasculature to determine the extent of vascular disease. In another embodiment, the vessel image is an image selected from the group consisting of an angiograph, a CT image, and an MRI. In yet another embodiment, the at least two parameters comprise parameters relating to volume and length from the vasculature of the vessel. In an additional embodiment, the calculation of a relationship between the at least two parameters is performed using a volume-length relation.

In at least one embodiment of a system for diagnosing vascular disease according to the present disclosure, the step of calculating a relationship between the at least two parameters is performed using a resistance-length and volume relation. In another embodiment, the at least two parameters comprise parameters relating to diameter and length from the vasculature of the vessel. In yet another embodiment, the calculation of a relationship between the at least two parameters is performed using a diameter-length relation.

In at least one embodiment of a system for diagnosing vascular disease according to the present disclosure, the at least two parameters comprise parameters relating to flow rate and diameter from the vasculature of the vessel. In another embodiment, the calculation of a relationship between the at least two parameters is performed using a flow rate-diameter relation. In yet another embodiment, the at least two parameters comprise parameters relating to resistance, length, and volume from the vasculature of the vessel. In an additional embodiment, the calculation of a relationship between the at least two parameters is performed using a resistance-length and volume relation.

In at least one embodiment of a system for diagnosing vascular disease according to the present disclosure, the at least two parameters comprise parameters relating to flow rate and length from the vasculature of the vessel. In another embodiment, the calculation of a relationship between the at least two parameters is performed using a flow rate-length relation. In yet another embodiment, the comparison of the one or more vasculature data points to data relative to a model vasculature is performed by graphically comparing said data points to data relative to a model vasculature to determine the extent of vascular disease by identifying graphical differences between said data points to data relative to a model vasculature. In an additional embodiment, the comparison of the one or more vasculature data points to data relative to a model vasculature is performed by comparing said data points to data relative to a model vasculature in table form to determine the extent of vascular disease by identifying numerically calculated differences between said data points to data relative to a model vasculature.

In at least one embodiment of a system for diagnosing vascular disease according to the present disclosure, the system further comprises a program stored upon the storage medium, said program operable by the processor upon data relative of measurements from a vasculature of a vessel. In another embodiment, the system comprises a user system and a server system, and wherein the user system and the server system are operably connected to one another.

In at least one embodiment of a system for diagnosing vascular disease in a patient's vascular tree according to the present disclosure, the system comprises a processor and a storage medium operably connected to the processor, the storage medium capable of receiving and storing data relative of measurements from a vasculature of a vessel, wherein the processor is operable to, generate a model vascular tree from a minimum energy hypothesis calculation, and compare the patient's vascular tree with the model vascular tree to determine the extent of vascular disease. In another embodiment, the generation of a model vascular tree from a minimum energy hypothesis calculation is performed by calculating a relationship between at least two parameters from at least two measurements to generate one or more model vasculature data points within the model vascular tree. In at least one embodiment of a system for diagnosing vascular disease in a patient's vascular tree according to the present disclosure, the at least two parameters comprise parameters relating to volume and length. In another embodiment, the calculation of a relationship between the at least two parameters is performed using a volume-length relation. In yet another embodiment, the calculation of a relationship between the at least two parameters is performed using a resistance-length and volume relation.

In at least one embodiment of a system for diagnosing vascular disease in a patient's vascular tree according to the present disclosure, the at least two parameters comprise parameters relating to diameter and length. In another embodiment, the calculation of a relationship between the at least two parameters is performed using a diameter-length relation. In yet another embodiment, the at least two parameters comprise parameters relating to flow rate and diameter. In an additional embodiment, the calculation of a relationship between the at least two parameters is performed using a flow rate-diameter relation.

In at least one embodiment of a system for diagnosing vascular disease in a patient's vascular tree according to the present disclosure, the at least two parameters comprise parameters relating to resistance, length, and volume. In another embodiment, the calculation of a relationship between the at least two parameters is performed using a resistance-length and volume relation. In yet another embodiment, the at least two parameters comprise parameters relating to flow rate and length. In an additional embodiment, the calculation of a relationship between the at least two parameters is performed using a flow rate-length relation.

In at least one embodiment of a system for diagnosing vascular disease in a patient's vascular tree according to the present disclosure, the comparison of the patient's vascular tree with the model vascular tree to determine the extent of vascular disease is performed by graphically comparing the patient's vascular tree with the model vascular tree to determine the extent of vascular disease by identifying graphical differences between the patient's vascular tree with the model vascular tree. In another embodiment, the comparison of the patient's vascular tree with the model vascular tree to determine the extent of vascular disease is performed by comparing the patient's vascular tree with the model vascular tree in table form to determine the extent of vascular disease by identifying numerically calculated differences between the patient's vascular tree with the model vascular tree. In yet another embodiment, the system further comprises a program stored upon the storage medium, said program operable by the processor upon data relative of measurements from a vasculature of a vessel. In an additional embodiment, the system comprises a user system and a server system, and wherein the user system and the server system are operably connected to one another.

In at least one embodiment of a program having a plurality of program steps to be executed on a computer having a processor and a storage medium to analyze data relative of measurements from a vasculature of a vessel according to the present disclosure, the program is operable to obtain a vessel image showing a vasculature of a vessel, identify at least two measurements from the vasculature of the vessel, the measurements relating to at least two parameters, calculate a relationship between the at least two parameters from the at least two measurements to generate one or more vasculature data points, and compare the one or more vasculature data points to data relative to a model vasculature to determine the extent of vascular disease.

In at least one embodiment of a program having a plurality of program steps to be executed on a computer having a processor and a storage medium to analyze data relative of measurements from a vasculature of a vessel according to the present disclosure, the program is operable to generate a model vascular tree from a minimum energy hypothesis calculation, and compare the patient's vascular tree with the model vascular tree to determine the extent of vascular disease.

In at least one embodiment of a method to design an energy efficient microfluidic channel device according to the present disclosure, the method comprises the steps of identifying at least two parameters relating to a desired microfluidic channel device, calculating a relationship between the at least two parameters to generate at least two measurements, and utilizing the at least two measurements to design the microfluidic channel device. In another embodiment, the at least two parameters comprise parameters relating to volume and length of a desired microfluidic channel device. In yet another embodiment, the step of calculating a relationship between the at least two parameters is performed using a volume-length relation. In an additional embodiment, the step of calculating a relationship between the at least two parameters is performed using a resistance-length and volume relation.

In at least one embodiment of a method to design an energy efficient microfluidic channel device according to the present disclosure, the at least two parameters comprise parameters relating to diameter and length. In another embodiment, the step of calculating a relationship between the at least two parameters is performed using a diameter-length relation. In yet another embodiment, the at least two parameters comprise parameters relating to flow rate and diameter. In an additional embodiment, the step of calculating a relationship between the at least two parameters is performed using a flow rate-diameter relation.

In at least one embodiment of a method to design an energy efficient microfluidic channel device according to the present disclosure, the at least two parameters comprise parameters relating to resistance, length, and volume. In another embodiment, the step of calculating a relationship between the at least two parameters is performed using a resistance-length and volume relation. In yet another embodiment, the at least two parameters comprise parameters relating to flow rate and length. In an additional embodiment, the step of calculating a relationship between the at least two parameters is performed using a flow rate-length relation.

In at least one embodiment of a method to design an energy efficient microfluidic channel device according to the present disclosure, the method further comprises the step of utilizing the at least two measurements to fabricate the microfluidic channel device.

A model vascular tree was derived from examining many normal patients, thereby establishing a normal trend, and then diagnosing disease as a function of variation from the statistical norm of this model vascular tree.

DETAILED DESCRIPTION

The disclosure of the present application applies concepts from biomimetics and microfluidics to analyze vascular tree structure, thus improving the efficacy and accuracy of diagnostics involving vascular diseases such as DCAD. Scaling laws are developed in the form of equations that use the relationships between arterial volume, cross-sectional area, blood flow and the distal arterial length to quantify moderate levels of diffuse coronary artery disease. For the purposes of promoting an understanding of the principles of the present disclosure, reference will now be made to the embodiments illustrated in the drawings, and specific language will be used to describe the same. It will nevertheless be understood that no limitation of the scope of the present disclosure is thereby intended.

Biomimetics (also known as bionics, biognosis, biomimicry, or bionical creativity engineering) is defined as the application of methods and systems found in nature to the study and design of engineering systems and modern technology. The mimic of technology from nature is based on the premise that evolutionary pressure forces natural systems to become highly optimized and efficient. Some examples include (1) the development of dirt- and water-repellent paint from the observation that the surface of the lotus flower plant is practically unsticky, (2) hulls of boats imitating the thick skin of dolphins, and (3) sonar, radar, and medical ultrasound imaging imitating the echolocation of bats.

Microfluidics is the study of the behavior, control and manipulation of microliter and nanoliter volumes of fluids. It is a multidisciplinary field comprising physics, chemistry, engineering and biotechnology, with practical applications to the design of systems in which such small volumes of fluids may be used. Microfluidics is used in the development of DNA chips, micro-propulsion, micro-thermal technologies, and lab-on-a-chip technology.

Regarding the minimum energy hypothesis, the architecture (or manifolds) of the transport network is essential for transport of material in microfluid channels for various chips. The issue is how to design new devices, and more particularly, how to fabricate microfluidic channels that provide a minimum cost of operation. Nature has developed optimal channels (or transport systems) that utilize minimum energy for transport of fluids. The utility of nature's design of transport systems in engineering applications is an important area of biomimetics.

Biological trees (for example, vascular trees) are either used to conduct fluids such as blood, air, bile or urine. Energy expenditure is required for the conduction of fluid through a tree structure because of frictional losses. The frictional losses are reduced when the vessel branches have larger diameters. This comes with a cost, however, for the metabolic construction and maintenance of the larger volume of the structure. The question is what physical or physiological factors dictate the design of vascular trees. The answer is that the design of vascular trees obeys the "minimum energy hypothesis", i.e., the cost of construction and operation of the vascular system appears to be optimized.

The disclosure of the present application is based on a set of scaling laws determined from a developed minimum energy hypothesis. Equation #1 (the "volume-length relation") demonstrates a relationship between vessel volume, the volume of the entire crown, vessel length, and the cumulative vessel length of the crown:

$$\frac{V}{V_{max}} = \left(\frac{L}{L_{max}}\right)^{\frac{5}{\epsilon'+1}} \quad (1)$$

In Equation #1, V represents the vessel volume, $V_{max}$ the volume of the entire crown, L represents the vessel length, $L_{max}$ represents the cumulative vessel length of the entire crown, and $\epsilon'$ represents the crown flow resistance, which is equal to the ratio of metabolic to viscous power dissipation.

Equation #2 (the "diameter-length relation") demonstrates a relationship between vessel diameter, the diameter of the most proximal stem, vessel length, and the cumulative vessel length of the crown:

$$\frac{D}{D_{max}} = \left(\frac{L}{L_{max}}\right)^{\frac{3\epsilon'-2}{4(\epsilon'+1)}} \quad (2)$$

In Equation #2, D represents the vessel diameter, $D_{max}$ represents the diameter of the most proximal stem, L represents the vessel length, $L_{max}$ represents the cumulative vessel length of the entire crown, and $\epsilon'$ represents the crown flow resistance, which is equal to the ratio of metabolic to viscous power dissipation.

Equation #3 (the "flow rate-diameter relation") demonstrates a relationship between the flow rate of a stem, the flow rate of the most proximal stem, vessel diameter, and the diameter of the most proximal stem:

$$\frac{Q}{Q_{max}} = \left(\frac{D}{D_{max}}\right)^{\frac{4(\epsilon'+1)}{3\epsilon'-2}} \quad (3)$$

In Equation #3, Q represents flow rate of a stem, $Q_{max}$ represents the flow rate of the most proximal stem, V represents vessel diameter, $V_{max}$ represents the diameter of the most proximal stem, and $\epsilon'$ represents the crown flow resistance, which is equal to the ratio of metabolic to viscous power dissipation.

Regarding the aforementioned Equations, a vessel segment is referred to as a "stem," and the entire tree distal to the stem is referred as a "crown." The aforementioned parameters relate to the crown flow resistance and is equal to the ratio of maximum metabolic-to-viscous power dissipation.

Two additional relations were found for the vascular trees. Equation #4 (the "resistance-length and volume relation") demonstrates a relationship between the crown resistance, the resistance of the entire tree, vessel length, the cumulative vessel length of the crown, vessel volume, and the volume of the entire crown:

$$\frac{R_c}{R_{max}} = \frac{(L/L_{max})^3}{(V/V_{max})^{\epsilon''}} \quad (4)$$

In Equation #4, $R_c$ represents the crown resistance, $R_{max}$ represents the resistance of the entire tree, L represents vessel length, $L_{max}$ represents the cumulative vessel length of the entire crown, V represents vessel volume, $V_{max}$ represents the volume of the entire crown, and $\epsilon'$ represents the crown flow resistance, which is equal to the ratio of metabolic to viscous power dissipation. Resistance, as referenced herein, is defined as the ratio of pressure differenced between inlet and outlet of the vessel.

Equation #5 (the "flow rate-length relation") demonstrates a relationship between the flow rate of a stem, the flow rate of the most proximal stem, vessel length, the cumulative vessel length of the entire crown:

$$\frac{Q}{Q_{max}} = \frac{L}{L_{max}} \quad (5)$$

In Equation #5, Q represents flow rate of a stem, $Q_{max}$ represents the flow rate of the most proximal stem, L represents vessel length, and $L_{max}$ represents the cumulative vessel length of the entire crown.

In at least one embodiment of the disclosure of the present application, the application of one or more of the aforementioned Equations to acquired vessel data may be useful diagnose and/or aid in the diagnosis of disease.

By way of example, the application of one or more of the aforementioned Equations are useful to diagnose DCAD. For such a diagnosis, the applications of Equations #1-#3 may provide the "signatures" of normal vascular trees and impart a rationale for diagnosis of disease processes. The self-similar nature of these laws implies that the analysis can be carried out on a partial tree as obtained from an angiogram, a computed tomography (CT) scan, or an magnetic resonance imaging (MRI). Hence, the application of these Equations to the obtained images may serve for diagnosis of vascular disease that affect the lumen dimension, volume, length (vascularity) or perfusion (flow rate). Additionally, the fabrication of the microfluidic channels can be governed by Equations #1-#5 to yield a system that requires minimum energy of construction and operation. Hence, energy requirements will be at a minimum to transport the required microfluidics.

Figure 1:
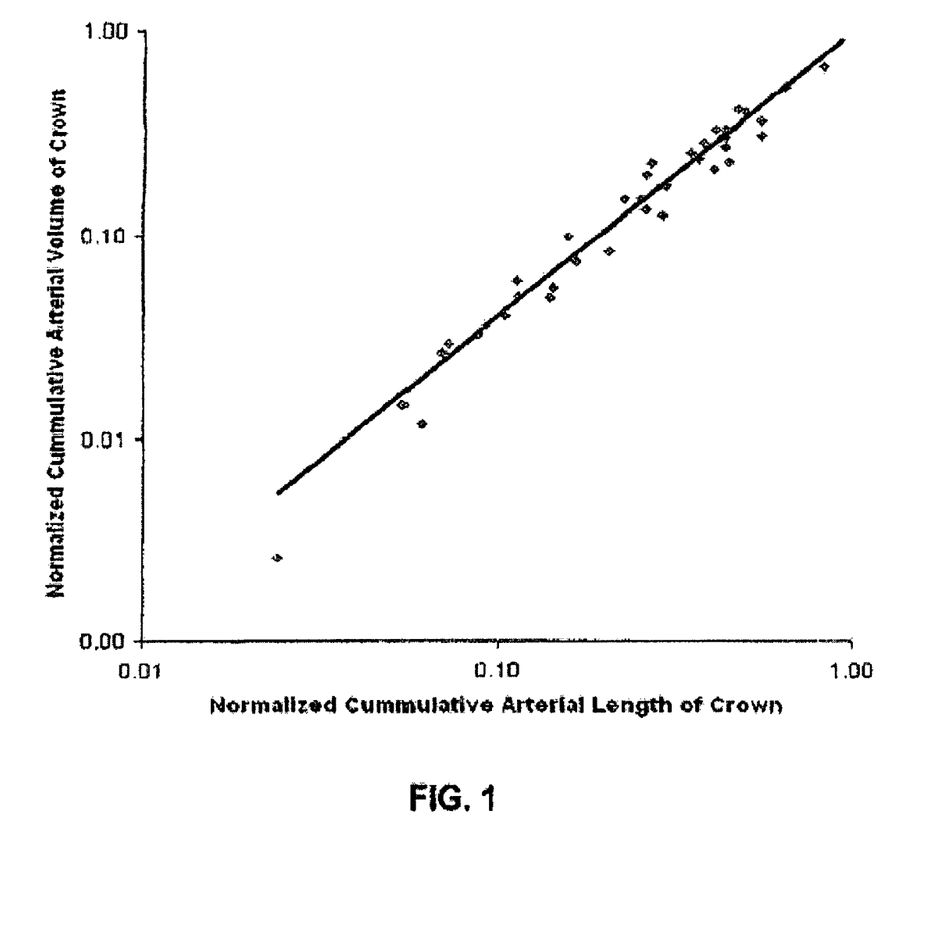
FIG. 1 shows the relation between normalized cumulative arterial volume and corresponding normalized cumulative arterial length for each crown on a log-log plot, according to at least one embodiment of the present disclosure.

In one exemplary embodiment, the application of the volume-length relation (Equation #1) to actual obtained images is considered as shown in FIG. 1. First, images (angiograms in this example) of swine coronary arteries were obtained. The application of Equation #1 on various volumes and lengths from the angiograms resulted in the individual data points shown within FIG. 1 (on a logarithmic scale). The line depicted within FIG. 1 represents the mean of the data points (the best fit) among the identified data points.

Figure 2:
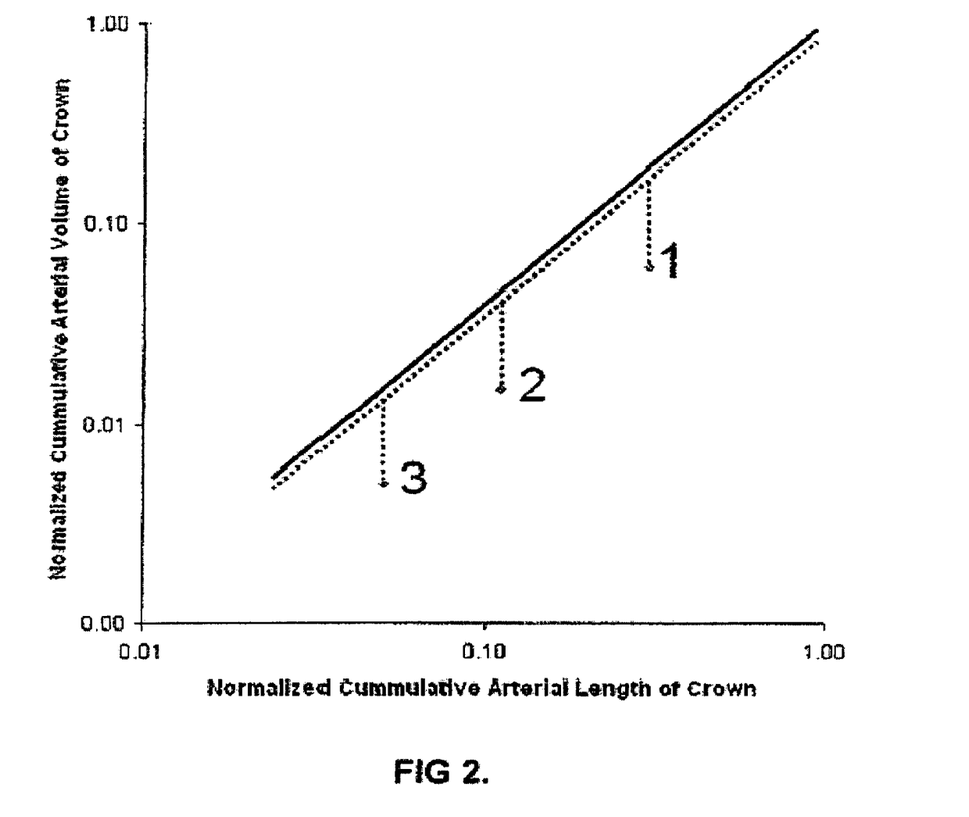
FIG. 2 shows the presence of DCAD at locations along the mean trend lines for normal (solid) and DCAD vasculature (broken) according to at least one embodiment of the present disclosure.

In FIG. 2, the mean of the data (solid line) is compared to an animal with diffuse disease at three different vessel sizes: proximal (1), middle (2), and distal (3). The reductions in volume shown on FIG. 2 correspond to approximately 40% stenosis, which is typically undetectable with current methodologies. At each diffuse stenosis, the length remains constant but the diameter (cross-sectional, and hence, volume) changes. The length is unlikely to change unless the flow becomes limiting (more than approximately 80% stenosis) and the vascular system experiences vessel loss (rarefication) and remodeling. It is clear that a 40% stenosis deviates significantly from the y-axis (as determined by statistical tests) from the normal vasculature, and as such, 40% stenosis can be diagnosed by the system and method of the disclosure of the present application. It can be appreciated that the disclosure of the present application can predict inefficiencies as low as about 10%, compared to well-trained clinicians who can only predict inefficiencies at about 60% at best.

This exemplary statistical test compares the deviation of disease to normality relative to the variation within normality. The location of the deviation along the x-axis corresponds to the size of the vessel. The vessel dimensions range as proximal>mid>distal. Hence, by utilizing the system and method of the disclosure of the present application, the diagnosis of the extent of disease and the dimension of the vessel branch is now possible. Similar embodiments with other scaling relations as described herein can be applied similarly to model and actual vascular data.

The techniques disclosed herein have tremendous application in a large number of technologies. For example, a software program or hardware device may be developed to diagnose the percentage of inefficiency (hence, occlusion) in a circulatory vessel or system.

Figure 3:
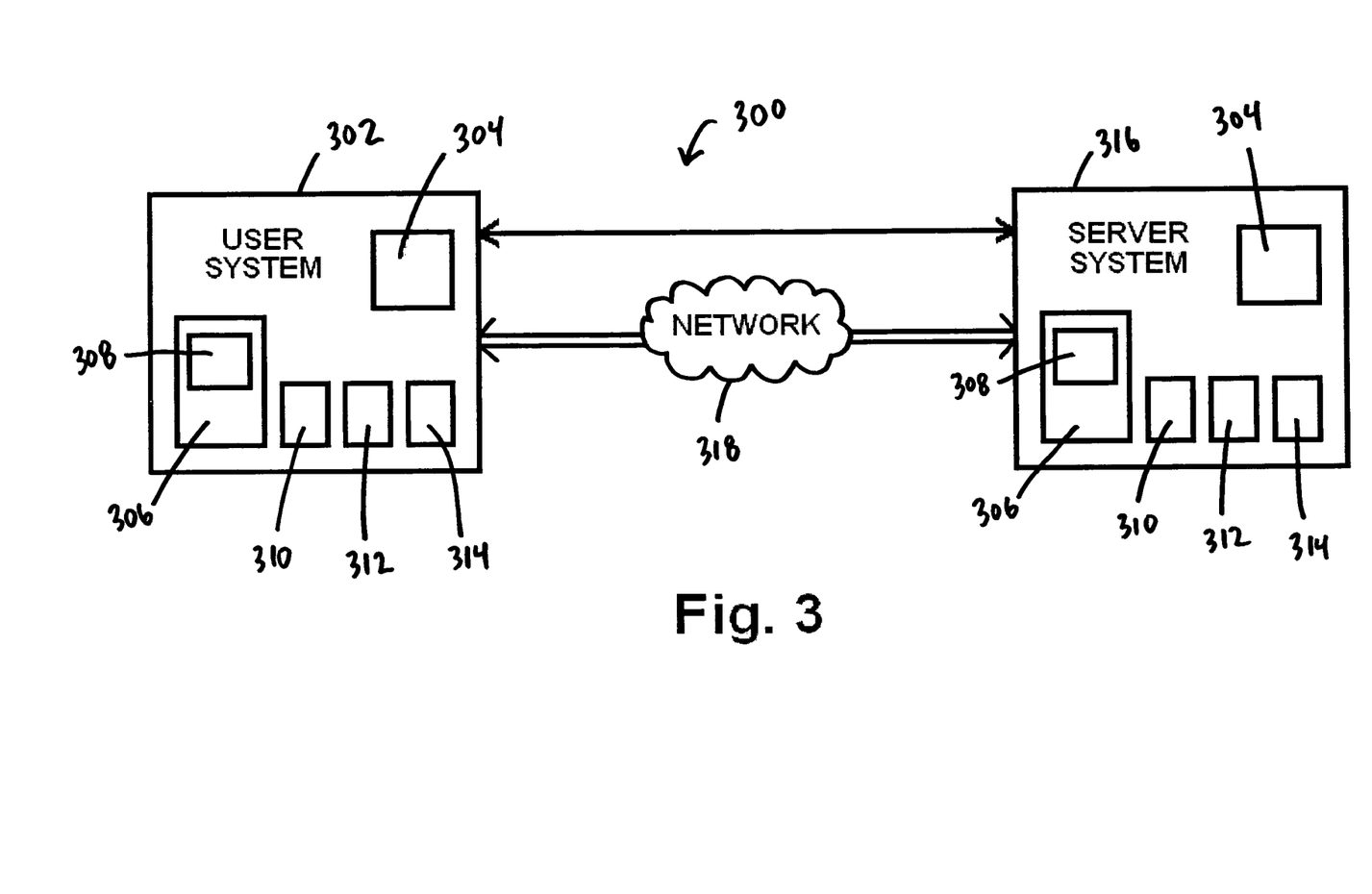
FIG. 3 shows a diagnostic system according to at least one embodiment of the present disclosure.

Regarding the computer-assisted determination of such diagnoses, an exemplary system of the disclosure of the present application is provided. Referring now to FIG. 3, there is shown a diagrammatic view of an embodiment of diagnostic system 300 of the present disclosure. In the embodiment shown in FIG. 3, diagnostic system 300 comprises user system 302. In this exemplary embodiment, user system 302 comprises processor 304 and one or more storage media 306. Processor 304 operates upon data obtained by or contained within user system 302. Storage medium 306 may contain database 308, whereby database 308 is capable of storing and retrieving data. Storage media 306 may contain a program (including, but not limited to, database 308), the program operable by processor 304 to perform a series of steps regarding data relative of vessel measurements as described in further detail herein.

Any number of storage media 306 may be used with diagnostic system 300 of the present disclosure, including, but not limited to, one or more of random access memory, read only memory, EPROMs, hard disk drives, floppy disk drives, optical disk drives, cartridge media, and smart cards, for example. As related to user system 302, storage media 306 may operate by storing data relative of vessel measurements for access by a user and/or for storing computer instructions. Processor 304 may also operate upon data stored within database 308.

Regardless of the embodiment of diagnostic system 300 referenced herein and/or contemplated to be within the scope of the present disclosure, each user system 302 may be of various configurations well known in the art. By way of example, user system 302, as shown in FIG. 3, comprises keyboard 310, monitor 312, and printer 314. Processor 304 may further operate to manage input and output from keyboard 310, monitor 312, and printer 314. Keyboard 310 is an exemplary input device, operating as a means for a user to input information to user system 302. Monitor 312 operates as a visual display means to display the data relative of vessel measurements and related information to a user using a user system 302. Printer 314 operates as a means to display data relative of vessel measurements and related information. Other input and output devices, such as a keypad, a computer mouse, a fingerprint reader, a pointing device, a microphone, and one or more loudspeakers are contemplated to be within the scope of the present disclosure. It can be appreciated that processor 304, keyboard 310, monitor 312, printer 314 and other input and output devices referenced herein may be components of one or more user systems 302 of the present disclosure.

It can be appreciated that diagnostic system 300 may further comprise one or more server systems 316 in bidirectional communication with user system 302, either by direct communication (shown by the single line connection on FIG. 3), or through a network 318 (shown by the double line connections on FIG. 3) by one of several configurations known in the art. Such server systems 316 may comprise one or more of the features of a user system 302 as described herein, including, but not limited to, processor 304, storage media 306, database 308, keyboard 310, monitor 312, and printer 314, as shown in the embodiment of diagnostic system 300 shown in FIG. 3. Such server systems 316 may allow bidirectional communication with one or more user systems 302 to allow user system 302 to access data relative of vessel measurements and related information from the server systems 316. It can be appreciated that a user system 302 and/or a server system 316 referenced herein may be generally referred to as a "computer."

The disclosure of the present application also relates to the design and fabrication of micro-fluidic chambers for use in research and development, thereby designing a chamber that maximizes flow conditions while minimizing the amount of material needed to construct the chamber. Many other uses are also possible and within the scope of the disclosure of the present application.

The foregoing disclosure of the exemplary embodiments of the present application has been presented for purposes of illustration and description and can be further modified within the scope and spirit of this disclosure. It is not intended to be exhaustive or to limit the present disclosure to the precise forms disclosed. This application is therefore intended to cover any variations, uses, or adaptations of a device, system and method of the present application using its general principles. Further, this application is intended to cover such departures from the present disclosure as may come within known or customary practice in the art to which this system of the present application pertains. Many variations and modifications of the embodiments described herein will be apparent to one of ordinary skill in the art in light of the above disclosure. The scope of the present disclosure is to be defined only by the claims appended hereto, and by their equivalents.

Further, in describing representative embodiments of the present disclosure, the specification may have presented the method and/or process of the present disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present disclosure should not be limited to the performance of their steps in the order written, and one skilled in the art can readily appreciate that the sequences may be varied and still remain within the spirit and scope of the present disclosure.

What is claimed is:

1. A method for diagnosing vascular disease, the method comprising the steps of:
    obtaining a vessel image showing a vasculature of a vessel having a vascular disease, the vasculature of the vessel including at least part of a biological tree having a stem and a crown;
    identifying at least two measurements from the vessel image, the measurements relating to at least two parameters selected from the group consisting of a vessel volume, a vessel length, a vessel diameter, a flow rate of a stem, and crown resistance;
    calculating at least two cumulative measurements corresponding to the selected at least two parameters, the at least two cumulative measurements selected from the group consisting of a volume of the crown corresponding to the vessel volume parameter, a cumulative vessel length of the crown corresponding to the vessel length parameter, a diameter of a most proximal stem corresponding to the vessel diameter parameter, a flow rate of a most proximal stem corresponding to the flow rate of the stem parameter, and a resistance of the biological tree corresponding to the crown resistance parameter;
    calculating a relationship between the at least two parameters from the at least two measurements and the at least two cumulative measurements to generate one or more vasculature data points using a processor operably connected to a storage medium having the at least two measurements stored thereon; and
    comparing the one or more vasculature data points to data relative to a model vasculature to determine the extent of vascular disease.

2. The method of claim 1, wherein the vessel image is an image selected from the group consisting of an angiograph, a computed tomography scan, and a magnetic resonance image.

3. The method of claim 1, wherein the at least two parameters comprise the vessel volume and the vessel length, and wherein the at least two cumulative measurements comprise the volume of the crown and the cumulative vessel length of the crown.

4. The method of claim 3, wherein the step of calculating a relationship between the at least two parameters is performed using a volume-length relation.

5. The method of claim 3, wherein the step of calculating a relationship between the at least two parameters is performed using a resistance-length and volume relation.

6. The method of claim 1, wherein the at least two parameters comprise the vessel diameter and the vessel length, and wherein the at least two cumulative measurements comprise the diameter of the most proximal stem and the cumulative vessel length of the crown.

7. The method of claim 6, wherein the step of calculating a relationship between the at least two parameters is performed using a diameter-length relation.

8. The method of claim 1, wherein the at least two parameters comprise the flow rate and the vessel diameter, and wherein the at least two cumulative measurements comprise the flow rate of the most proximal stem and the diameter of the most proximal stem.

9. The method of claim 8, wherein the step of calculating a relationship between the at least two parameters is performed using a flow rate-diameter relation.

10. The method of claim 1, wherein the at least two parameters comprise the crown resistance, the vessel length, and the vessel volume, and wherein the at least two cumulative measurements comprise the resistance of the biological tree, the cumulative vessel length of the crown, and the volume of the crown.

11. The method of claim 10, wherein the step of calculating a relationship between the at least two parameters is performed using a resistance-length and volume relation.

12. The method of claim 1, wherein the at least two parameters comprise the flow rate of the stem and the vessel length, and wherein the at least two cumulative measurements comprise the flow rate of the most proximal stem and the cumulative vessel length of the crown.

13. The method of claim 12, wherein the step of calculating a relationship between the at least two parameters is performed using a flow rate-length relation.

14. The method of claim 1, wherein the step of comparing the one or more vasculature data points to data relative to a model vasculature is performed by graphically comparing said data points to data relative to a model vasculature to determine the extent of vascular disease by identifying graphical differences between said data points to data relative to a model vasculature.

15. The method of claim 1, wherein the step of comparing the one or more vasculature data points to data relative to a model vasculature is performed by comparing said data points to data relative to a model vasculature in table form to determine the extent of vascular disease by identifying numerically calculated differences between said data points to data relative to a model vasculature.

16. A method for diagnosing vascular disease in a patient's vascular tree, the method comprising the steps of:
    generating a model vascular tree from a minimum energy hypothesis calculation using one or more scaling laws having at least two parameters selected from the group consisting of a vessel volume, a vessel length, a vessel diameter, a flow rate of a stem, and crown resistance, the model vascular tree generated using a processor operably connected to a storage medium having data relating to the one or more scaling laws stored thereon;

calculating a relationship between the at least two parameters from at least two model measurements to generate one or more model vasculature data points within the model vascular tree; and determining the extent of vascular disease, wherein the patient's vascular tree is obtained using the one or more scaling laws using at least two patient measurements relating to the at least two parameters as applied to a vessel image showing a vasculature of the patient's vessel having a vascular disease, the vasculature of the patient's vessel including at least part of the patient's vascular tree having a stem and a crown, the determining step comprising:

calculating at least two cumulative measurements corresponding to the selected at least two parameters, the at least two cumulative measurements selected from the group consisting of a volume of the crown corresponding to the vessel volume parameter, a cumulative vessel length of the crown corresponding to the vessel length parameter, a diameter of a most proximal stem corresponding to the vessel diameter parameter, a flow rate of a most proximal stem corresponding to the flow rate of the stem parameter, and a resistance of the biological tree corresponding to the crown resistance parameter;

calculating a relationship between the at least two parameters from the at least two patient measurements and the at least two cumulative measurements to generate one or more patient vasculature data points; and comparing the one or more patient vasculature data points to the one or more model vasculature data points to determine the extent of vascular disease.

17. The method of claim 16, wherein the at least two parameters comprise the vessel volume and the vessel length, and wherein the at least two cumulative measurements comprise the volume of the crown and the cumulative vessel length of the crown.

18. The method of claim 17, wherein the step of calculating a relationship between the at least two parameters from the at least two patient measurements and the at least two cumulative measurements is performed using a volume-length relation.

19. The method of claim 17, wherein the step of calculating a relationship between the at least two parameters from the at least two patient measurements and the at least two cumulative measurements is performed using a resistance-length and volume relation.

20. The method of claim 16, wherein the at least two parameters comprise the vessel diameter and the vessel length, and wherein the at least two cumulative measurements comprise the diameter of the most proximal stem and the cumulative vessel length of the crown.

21. The method of claim 20, wherein the step of calculating a relationship between the at least two parameters from the at least two patient measurements and the at least two cumulative measurements is performed using a diameter-length relation.

22. The method of claim 16, wherein the at least two parameters comprise the flow rate and the vessel diameter, and wherein the at least two cumulative measurements comprise the flow rate of the most proximal stem and the diameter of the most proximal stem.

23. The method of claim 22, wherein the step of calculating a relationship between the at least two parameters from the at least two patient measurements and the at least two cumulative measurements is performed using a flow rate-diameter relation.

24. The method of claim 16, wherein the at least two parameters comprise the crown resistance, the vessel length, and the vessel volume, and wherein the at least two cumulative measurements comprise the resistance of the biological tree, the cumulative vessel length of the crown, and the volume of the crown.

25. The method of claim 24, wherein the step of calculating a relationship between the at least two parameters from the at least two patient measurements and the at least two cumulative measurements is performed using a resistance-length and volume relation.

26. The method of claim 16, wherein the at least two parameters comprise the flow rate of the stem and the vessel length, and wherein the at least two cumulative measurements comprise the flow rate of the most proximal stem and the cumulative vessel length of the crown.

27. The method of claim 26, wherein the step of calculating a relationship between the at least two parameters from the at least two patient measurements and the at least two cumulative measurements is performed using a flow rate-length relation.

28. The method of claim 16, wherein the determining step is performed by graphically comparing the patient's vascular tree with the model vascular tree to determine the extent of vascular disease by identifying graphical differences between the patient's vascular tree with the model vascular tree.

29. The method of claim 16, wherein the determining step is performed by comparing the patient's vascular tree with the model vascular tree in table form to determine the extent of vascular disease by identifying numerically calculated differences between the patient's vascular tree with the model vascular tree.

30. A system for diagnosing vascular disease, the system comprising:

a computer processor;

a storage medium operably connected to the processor, the storage medium capable of receiving and storing data relative of measurements from a vasculature of a vessel;

wherein the processor is operable to:

obtain a vessel image showing a vasculature of a vessel having a vascular disease, the vasculature of the vessel including at least part of a biological tree having a stem and a crown;

identify at least two measurements from the vessel image, the measurements relating to at least two parameters selected from the group consisting of a vessel volume, a vessel length, a vessel diameter, a flow rate of a stem, and crown resistance;

calculate at least two cumulative measurements corresponding to the selected at least two parameters, the at least two cumulative measurements selected from the group consisting of a volume of the crown corresponding to the vessel volume parameter, a cumulative vessel length of the crown corresponding to the vessel length parameter, a diameter of a most proximal stem corresponding to the vessel diameter parameter, a flow rate of a most proximal stem corresponding to the flow rate of the stem parameter, and a resistance of the biological tree corresponding to the crown resistance parameter;

calculate a relationship between the at least two parameters from the at least two measurements and the at least two cumulative measurements to generate one or more vasculature data points; and compare the one or more vasculature data points to data relative to a model vasculature to determine the extent of vascular disease, wherein the extent of vascular disease is identified based upon a difference in the one or more vasculature data points in connection with one of the at least two parameters while another of the at least two parameters remains constant.

31. The system of claim 30, wherein the vessel image is an image selected from the group consisting of an angiograph, a computed tomography scan, and a magnetic resonance image.

32. The system of claim 30, wherein the at least two parameters comprise the vessel volume and the vessel length, and wherein the at least two cumulative measurements comprise the volume of the crown and the cumulative vessel length of the crown.

33. The system of claim 32, wherein the calculation of a relationship between the at least two parameters is performed using a volume-length relation.

34. The system of claim 32, wherein the step of calculating a relationship between the at least two parameters is performed using a resistance-length and volume relation.

35. The system of claim 30, wherein the at least two parameters comprise the vessel diameter and the vessel length, and wherein the at least two cumulative measurements comprise the diameter of the most proximal stem and the cumulative vessel length of the crown.

36. The system of claim 35, wherein the calculation of a relationship between the at least two parameters is performed using a diameter-length relation.

37. The system of claim 30, wherein the at least two parameters comprise the flow rate and the vessel diameter, and wherein the at least two cumulative measurements comprise the flow rate of the most proximal stem and the diameter of the most proximal stem.

38. The system of claim 37, wherein the calculation of a relationship between the at least two parameters is performed using a flow rate-diameter relation.

39. The system of claim 30, wherein the at least two parameters comprise the crown resistance, the vessel length, and the vessel volume, and wherein the at least two cumulative measurements comprise the resistance of the biological tree, the cumulative vessel length of the crown, and the volume of the crown.

40. The system of claim 39, wherein the calculation of a relationship between the at least two parameters is performed using a resistance-length and volume relation.

41. The system of claim 30, wherein the at least two parameters comprise the flow rate of the stem and the vessel length, and wherein the at least two cumulative measurements comprise the flow rate of the most proximal stem and the cumulative vessel length of the crown.

42. The system of claim 41, wherein the calculation of a relationship between the at least two parameters is performed using a flow rate-length relation.

43. The system of claim 30, wherein the comparison of the one or more vasculature data points to data relative to a model vasculature is performed by graphically comparing said data points to data relative to a model vasculature to determine the extent of vascular disease by identifying graphical differences between said data points to data relative to a model vasculature.

44. The system of claim 30, wherein the comparison of the one or more vasculature data points to data relative to a model vasculature is performed by comparing said data points to data relative to a model vasculature in table form to determine the extent of vascular disease by identifying numerically calculated differences between said data points to data relative to a model vasculature.

45. The system of claim 30, further comprising a program stored upon the storage medium, said program operable by the processor upon data relative of measurements from a vasculature of a vessel.

46. The system of claim 30, wherein the system comprises a user system and a server system, and wherein the user system and the server system are operably connected to one another.

47. A system for diagnosing vascular disease in a patient's vascular tree, the system comprising:
a computer processor; and
a storage medium operably connected to the processor, the storage medium capable of receiving and storing data relative of measurements from a vasculature of a vessel;
wherein the processor is operable to:
generate a model vascular tree from a minimum energy hypothesis calculation using one or more scaling laws having at least two parameters selected from the group consisting of a vessel volume, a vessel length, a vessel diameter, a flow rate of a stem, and crown resistance;
calculate a relationship between the at least two parameters from at least two model measurements to generate one or more model vasculature data points within the model vascular tree; and
determine the extent of vascular disease, wherein the patient's vascular tree is obtained using the one or more scaling laws using at least two patient measurements relating to the at least two parameters as applied to a vessel image showing a vasculature of the patient's vessel having a vascular disease, the vasculature of the patient's vessel including at least part of the patient's vascular tree having a stem and a crown, wherein the extent of vascular disease is identified based upon a difference in one or more vasculature data points in connection with one of the at least two parameters while another of the at least two parameters remains constant, and wherein the extent of the vascular disease is determined by:
calculating at least two cumulative measurements corresponding to the selected at least two parameters, the at least two cumulative measurements selected from the group consisting of a volume of the crown corresponding to the vessel volume parameter, a cumulative vessel length of the crown corresponding to the vessel length parameter, a diameter of a most proximal stem corresponding to the vessel diameter parameter, a flow rate of a most proximal stem corresponding to the flow rate of the stem parameter, and a resistance of the biological tree corresponding to the crown resistance parameter;
calculating a relationship between the at least two parameters from the at least two patient measurements and the at least two cumulative measurements to generate one or more patient vasculature data points; and comparing the one or more patient vasculature data points to the one or more model vasculature data points to determine the extent of vascular disease.

48. The system of claim 47, wherein the at least two parameters comprise the vessel volume and the vessel length, and wherein the at least two cumulative measurements comprise the volume of the crown and the cumulative vessel length of the crown.

49. The system of claim 48, wherein the calculation of a relationship between the at least two parameters from the at least two patient measurements and the at least two cumulative measurements is performed using a volume-length relation.

50. The system of claim 48, wherein the calculation of a relationship between the at least two parameters from the at least two patient measurements and the at least two cumulative measurements is performed using a resistance-length and volume relation.

51. The system of claim 47, wherein the at least two parameters comprise the vessel diameter and the vessel length, and wherein the at least two cumulative measurements comprise the diameter of the most proximal stem and the cumulative vessel length of the crown.

52. The system of claim 51, wherein the calculation of a relationship between the at least two parameters from the at least two patient measurements and the at least two cumulative measurements is performed using a diameter-length relation.

53. The system of claim 47, wherein the at least two parameters comprise the flow rate and the vessel diameter, and wherein the at least two cumulative measurements comprise the flow rate of the most proximal stem and the diameter of the most proximal stem.

54. The system of claim 53, wherein the calculation of a relationship between the at least two parameters from the at least two patient measurements and the at least two cumulative measurements is performed using a flow rate-diameter relation.

55. The system of claim 47, wherein the at least two parameters comprise the crown resistance, the vessel length, and the vessel volume, and wherein the at least two cumulative measurements comprise the resistance of the biological tree, the cumulative vessel length of the crown, and the volume of the crown.

56. The system of claim 55, wherein the calculation of a relationship between the at least two parameters from the at least two patient measurements and the at least two cumulative measurements is performed using a resistance-length and volume relation.

57. The system of claim 47, wherein the at least two parameters comprise the flow rate of the stem and the vessel length, and wherein the at least two cumulative measurements comprise the flow rate of the most proximal stem and the cumulative vessel length of the crown.

58. The system of claim 57, wherein the calculation of a relationship between the at least two parameters from the at least two patient measurements and the at least two cumulative measurements is performed using a flow rate-length relation.

59. The system of claim 47, wherein the determination of the extent of vascular disease is performed by graphically comparing the patient's vascular tree with the model vascular tree to determine the extent of vascular disease by identifying graphical differences between the patient's vascular tree with the model vascular tree.

60. The system of claim 47, wherein the determination of the extent of vascular disease is performed by comparing the patient's vascular tree with the model vascular tree in table form to determine the extent of vascular disease by identifying numerically calculated differences between the patient's vascular tree with the model vascular tree.

61. The system of claim 47, further comprising a program stored upon the storage medium, said program operable by the processor upon data relative of measurements from a vasculature of a vessel.

62. The system of claim 47, wherein the system comprises a user system and a server system, and wherein the user system and the server system are operably connected to one another.

* * * * *